United States Patent [19]
Pennisi et al.

[11] Patent Number: 4,714,526
[45] Date of Patent: Dec. 22, 1987

[54] SUPERCRITICAL FLUID EXTRACTION METHOD FOR MULTI-COMPONENT SYSTEMS

[75] Inventors: Kenneth Pennisi; Eldred Chimowitz, both of Rochester, N.Y.

[73] Assignee: The University of Rochester, Rochester, N.Y.

[21] Appl. No.: 26,603

[22] Filed: Mar. 17, 1987

Related U.S. Application Data

[63] Continuation of Ser. No. 743,339, Jun. 10, 1985, abandoned.

[51] Int. Cl.$^4$ .......................... B01D 3/34; C07C 3/20; C07C 51/44
[52] U.S. Cl. ........................................ 203/49; 203/62; 203/66; 203/67; 203/70; 203/77; 562/494; 568/868
[58] Field of Search .................. 203/49, 73, 77, 99, 203/67–70, 52, 62, 66; 568/868; 562/494, 493; 202/173

[56] References Cited

U.S. PATENT DOCUMENTS

| | | | |
|---|---|---|---|
| 3,806,619 | 4/1974 | Zosel | 203/49 |
| 3,969,196 | 7/1976 | Zosel | 203/49 |
| 4,349,415 | 9/1982 | deFilippi et al. | 203/14 |
| 4,375,387 | 3/1983 | deFilippi et al. | 202/169 |
| 4,437,938 | 3/1984 | Bhise et al. | 203/49 |
| 4,437,939 | 3/1984 | Bhise et al. | 203/49 |
| 4,539,425 | 9/1985 | Kleintjens et al. | 562/494 |
| 4,547,587 | 10/1985 | Kleintjens et al. | 562/494 |

OTHER PUBLICATIONS

Modell, M. et al.; Supercritical Fluid Regeneration of Activated Carbon.
McHugh, M. A. et al., High Pressure Fluid Phase Equilibria . . . , AICHE Annual ME (1981).
Krukonis, Val; Supercritical Fluid Fractionation–An Alternative . . . , AICHE Annual ME (1983).
VanAlsten, J. G. et al.; Supercritical Enhancement Factors . . . , Paper 84a, AICHE Annual ME, 1984.
Kurnik, R. T. et al.; Solubility of Solids in Supercritical . . . , J. Chem. Eng. Data, 26:47 (1981).
Kurnik, R. T., and Reid, R. C.; Solubility of Solid Mixtures . . . , Fluid Phase Equilibria, p. 93 (1982).

*Primary Examiner*—Wilbur Bascomb
*Attorney, Agent, or Firm*—Martin Lukacher

[57] ABSTRACT

A process for extracting pure components from a multi-component system, said system comprising a mixture of at least two solids or liquids in a supercritical fluid at constant pressure, which involves making use of the cross-over pressure points of the components which comprise the system.

30 Claims, 10 Drawing Figures

SUPERCRITICAL FLUID EXTRACTION METHOD FOR MULTI-COMPONENT SYSTEMS

This is a continuation, of application Ser. No. 743,339, filed June 10, 1985, now abandoned.

This invention relates to methods for extracting pure components from a multi-component system which consists of mixtures of components.

The invention is especially suitable for use in the extraction of pure components from a system containing a plurality of different solids or liquids dissolved in a supercritical fluid at constant pressure, which involves making use of the cross-over pressure points of the components which comprise the system.

Supercritical fluids are gaseous compounds which at temperatures and pressures above their critical temperature and pressure behave as fluids. Such supercritical fluids tend to be pure compounds; however, they may be "doped" with small amounts of entrainer compounds to improve their selectivity. Compounds that may function as supercritical fluids are well known in the art and include, but are not limited to: hydrocarbons, such as methane, ethane, propane; halogenated hydrocarbons, such as halomethanes and haloethanes; and inorganics, such as carbon dioxide, nitrous oxide, sulfur dioxide and ammonia.

The importance of supercritical fluids lies in their known ability to dissolve materials of low volatility. As a result, extraction using supercritical fluids is a useful separation technique. Kurnik and Reid, Fluid Phase Equilibria, 8:93–97 (1982), provides an introduction and discussion to the behavior of supercritical fluids as a solvent.

In practice, the use of a supercritical fluid as a solvent has involved essentially two types of applications. The first of such applications is described by Kurnik and Reid for ternary systems (i.e., a mixture of $solid_1$—$solid_2$—supercritical fluid). In general, they note that the selectivity of a solvent (or the solvation power of the solvent with respect to a particular solute) at low pressure is a function solely of the vapor pressures of the two solids. Thus, the ratio of $solid_1$ to $solid_2$ in the solvent will be equal to the ratio of the vapor pressures.

At the high pressures at which supercritical fluids exist, solvent selectivity approaches some limiting value. In such a system, $solid_1$ is drawn off in a fixed proportion to $solid_2$. The problem, however, is that once the solid mixture is precipitated out of the solvent no further refinement is possible under these conditions; thus, one is left with a "purity" dependent upon and limited by the selectivity ratio. Thus, the process of Kurnik and Reid will lead to an "azetropic" situation where the mixture purity is limited by the selectivity ratio. In addition, the ratio will differ as the components in the mixture differ.

The second of the applications achieves a higher degree of purity than obtained by Kurnik and Reid, but involves the additional step of distillation to achieve purity. Such a system has been described by deFilippi. See deFilippi, et al., U.S. Pat. No. 4,375,387 (Apparatus For Separation Organic Liquid Solutes From Their Solvent Mixtures) and U.S. Pat. No. 4,349,415 (Process For Separation Organic Liquid Solutes From Their Solvent Mixtures).

deFilippi's system is designed as a two-step process for separating organic solutes from an aqueous solution. The preferred embodiment of the system contemplates, as a first step, the separation of solute from the solution by passage of near-critical liquid carbon dioxide through the solution. This step leaves two components: solution with minor amounts of solute and solute in the extraction liquid. The second step is to depressurize the solute/liquid mixture to provide a two phase still feed. The still then is run to produce overhead and bottoms which comprise the extraction liquid and organic solute respectively.

Although deFilippi claims the use of supercritical carbon dioxide, the process essentially is geared to near-critical liquids. The behavior of such liquids differs radically from supercritical fluids. Distillation of product also is a requirement of deFilippi's process, and thus, it is disadvantageous because of the number of steps involved and the complexity of hardware and process controls required for distillation.

The present invention avoids the disadvantages both of deFilippi and of Kurnik and Reid by relying upon a single feature of supercritical fluids not previously appreciated for multi-component systems. The failure of the art to appreciate this feature will be apparent from Van Alsten, et al., Paper 84a (presented at the AICHE Annual Meeting, November 28, 1984) who stated: "[f]or an optimal supercritical separation scheme, it would be desirable to have systems in which the enhancement factor versus density lines diverged, that is, to have one solute increased in solubility while another is reduced. Unfortunately, even for systems whose difference in enhancement is high, the ratio of enhancement factors is nearly constant over the entire pressure (density) range. ... [U]sing a pure fluid would be inadequate to perform separations of these kinds." Contrary to Van Alsten's conclusions, such separation is possible. Applicants' invention solves these disadvantages through the use of cross-over pressure points exhibited by the various components of a multi-component system.

Briefly described, the invention provides an improved process for extracting pure components from a multi-component system by effecting a change in temperature at a pressure between the cross-over pressure points of the various components of the system.

A feature of this invention is that it can be extended to any multi-component system that exhibits separate cross-over pressure points for its components.

An advantage of this invention is that it is independent of distillation processes.

A further advantage of this invention is that it it is not limited to solid multi-component systems, and therefore, may be applied to liquids or liquid-solid systems where the components exhibit separate cross-over pressure points.

The objects, features and advantages of the invention, as well as the best known mode for practice thereof, will become more apparent from a reading of the following detailed description which makes reference to the following drawings:

FIG. 5 (a), (b) are flow charts of alternate processes by which pure components can be separated in a quaternary system;

To appreciate the advantage of this invention, it is important to understand the solubility behavior of pure compounds in a supercritical fluid as a function of pressure at a constant temperature. One of the interesting features of such solubility isotherms for pure compounds, be they solid or liquid, is the existence of a cross-over pressure point. This cross-over pressure is a point on the solubility diagram at which the various isotherms cross, and for many pure substances, experimental data show the cross-over point to be focussed around a quite distinct pressure. Thus, two compounds in the same supercritical fluid may exhibit different cross-over pressure points. The use of this property is important to the invention. Determining where such pressure points lie for any compound is straightforward and within the ordinary skill of those in the art.

Furthermore, for the same compound in different supercritical fluids, these cross-over pressures also can be significantly different. For example, 2,3 dimethylnaphthalene in ethylene has a cross-over pressure of 120 bars, while in carbon dioxide the cross-over pressure is 145 bars.

For pure compounds, the cross-over point also is rather unique with respect to temperature. Below the cross-over pressure an increase in temperature causes a decrease in solubility in the gas phase while above the cross-over pressure the opposite effect occurs. This is an unusual phenomenon that does not exist in liquid solvents at usual liquid extraction conditions. The accepted explanation for this phenomenon rests on the following observations. Below the cross-over point, the relative change in the density of the gas phase is more sensitive to temperature changes than is the case at higher pressures. This can be observed from a density plot of a supercritical fluid at various reduced temperatures and pressures.

Solubility of the solute in the gas phase depends strongly upon the solvent density and the vapor pressure of the solute. At pressures below the cross-over point, a decrease in temperature causes a decrease in solute vapor pressure and a strong increase in solvent density. The density effect predominates, hence the solubility of the solute increases with a temperature decrease. At pressures above the cross-over pressure, the vapor pressure effect predominates, hence a decrease in temperature causes a decrease in solubility.

Figure 1:
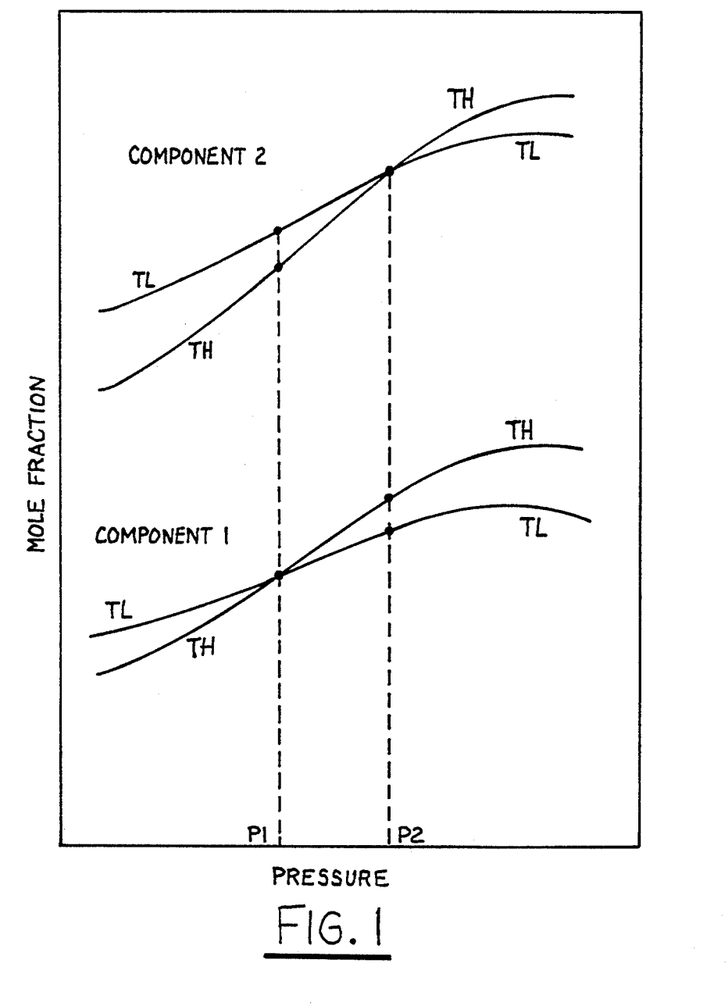
FIG. 1 is a theoretical plot of solubility of two components in a supercritical fluid at two temperatures as a function of pressure.

The existence of cross-over points in binary gas phase systems (i.e., one solid or liquid in a supercritical fluid) is known, but is of little import beyond theoretical practice. The existence of cross-over points in multi-component gas phase systems has not been appreciated as a simplified, commercially viable method for extraction. FIG. 1 illustrates the phenomenon graphically with two components in the gas phase of a supercritical solvent.

Figure 2:
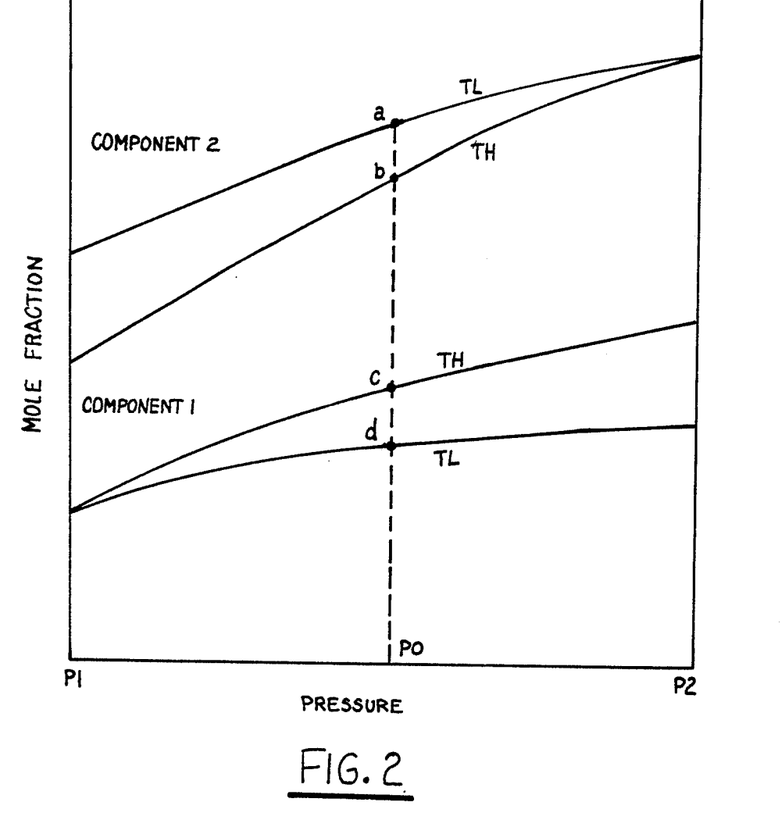
FIG. 2 is an enlarged portion of the plot shown in FIG. 1 between $P_1$ and $P_2$.

The cross-over pressures, considered to be separate for each component in the gas phase, are clearly shown as pressures $P_1$ and $P_2$. It is the pressure regime between $P_1$ and $P_2$ that is the primary focus of this invention. This regime is shown in an expanded form in FIG. 2.

At a pressure $P_0$, intermediate to $P_1$ and $P_2$, consider that the gas phase is initially at a temperature $T_H$ (with $T_H$ being greater than $T_L$) and then is cooled to a temperature $T_L$. For component 2, this is a process from b to a in FIG. 2, and clearly the equilibrium solubility of component 2 in the gas phase increases while the solubility of component 1 decreases in going from c to d. Hence, a process exists where, in a mixture of components 1 and 2, extraction at a pressure $P_0$ and temperature $T_H$, pure component 1 drops out of the gas phase by a simple temperature decrease to $T_L$. To complete the separation process, the temperature of the gas phase is raised to greater than $T_H$ at which point pure component 2 drops out of the gas phase.

Figure 3:
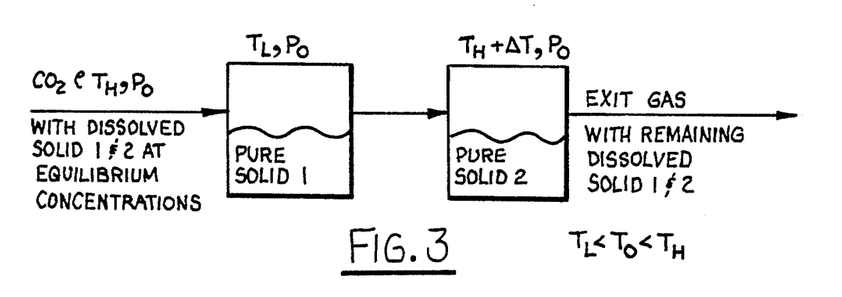
FIG. 3 is a flow chart of the process by which pure components can be separated in a ternary system.

The entire process is schematically diagrammed in FIG. 3. A supercritical fluid is passed through an initial chamber (not shown) containing a mixture of components 1 and 2 at a pressure $P_0$ and temperature $T_H$. Both components 1 and 2 are taken up into the gas phase. Regardless of the selectivity of the solvent, pure component 1 (having the lower cross-over pressure) will drop out of the gas phase into a first collection chamber when the temperature is reduced to $T_L$. A second collection chamber then can be used to collect pure component 2 when the temperature is raised to greater than $T_H$. The gas can then be directly returned to the first chamber upon reheating or the gas can go into another system for processing (e.g., distillation).

Figure 4:
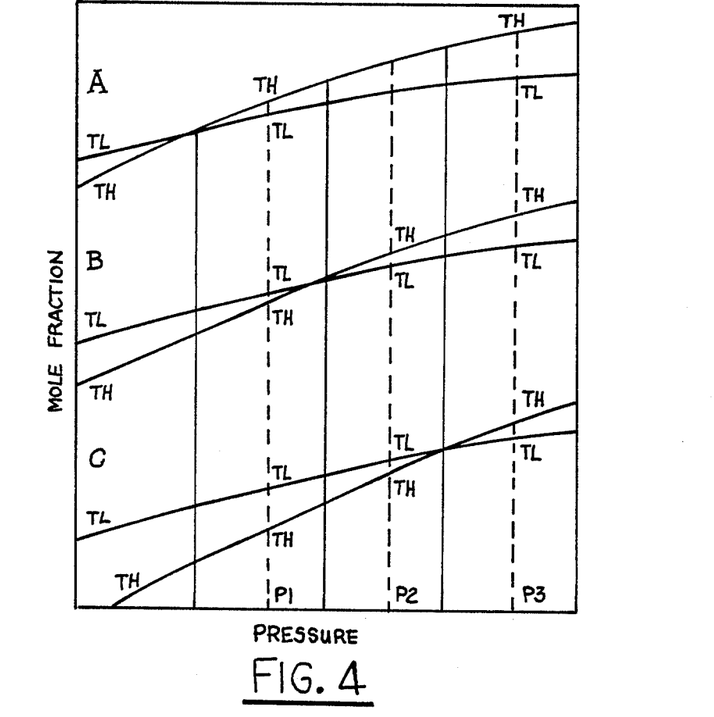
FIG. 4 is a theoretical plot, similar to FIG. 1 for a three component (quaternary) system.

The process described above for a ternary (i.e., two solids or liquids in a supercritical fluid) gas phase system can be extended to encompass more components. The relevant diagram for a quaternary mixture exhibiting three cross-over points is shown in FIG. 4 for the components A, B, C. The process for the separation of the initial mixture into pure components is schematically diagrammed in FIG. 5.

Figure 5A:
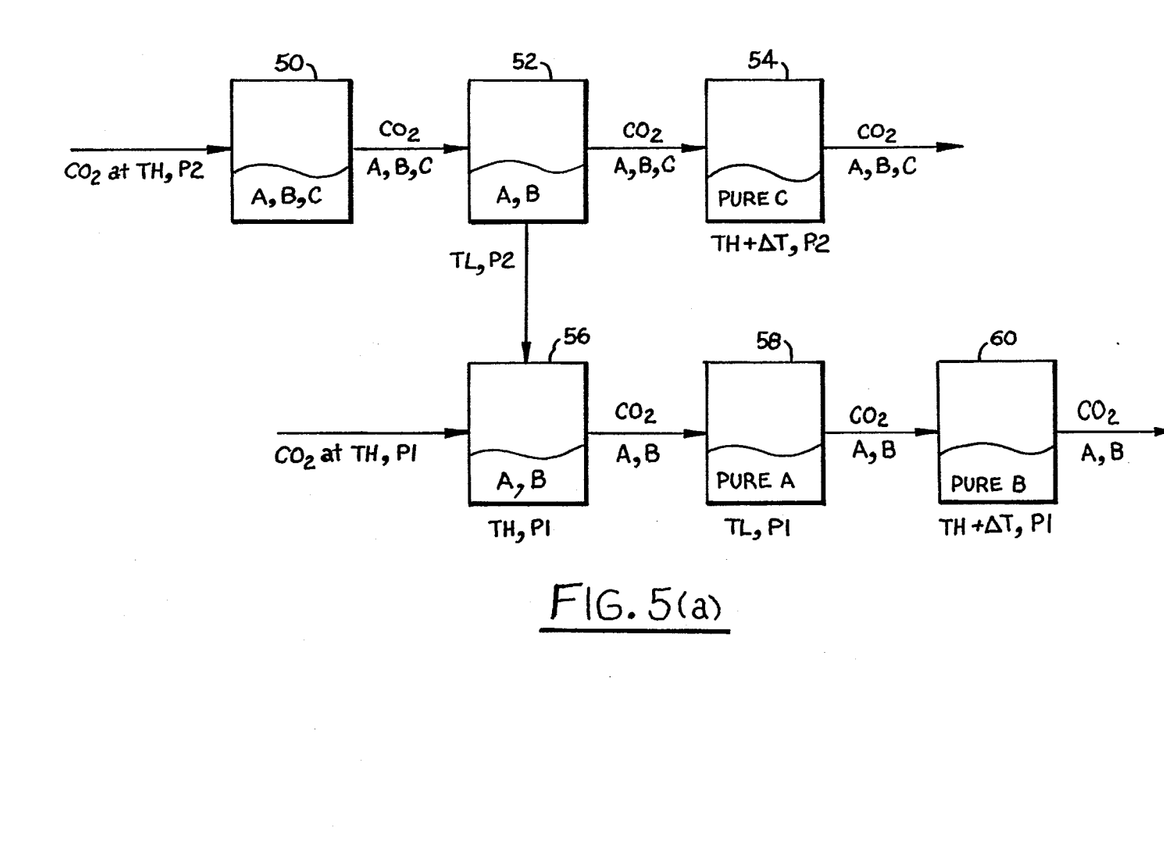

Preferredly, referring to FIG. 5(a), supercritical fluid at a temperature $T_H$ and pressure $P_2$ is contacted with a mixture of A, B and C in a first chamber 50 resulting in a fluid-component mixture. In a second chamber 52, the mixture is cooled to a temperature $T_L$. From FIG. 4, it will be seen that since $P_2$ is in the cross-over regime separating components (A,B) and C, a mixture predominantly of A and B will precipitate out leaving an exit gas rich in C (with reduced amounts of A and B). Passing the exit gas into a third chamber 54 and heating to temperature $T_H + \Delta T$ will cause only component C to deposit in the third chamber. Heating to $T_H + \Delta T$, where $\Delta T$ is an incremental temperature factor, insures that only the desired component will deposit. $\Delta T$ must be greater than $\Delta T = 0$. $\Delta T$ will be system dependent, and in the system described below for decanediol--benzoic acid, $\Delta T$ is less than 20° K.

Components A and B, deposited in the second chamber 52, can be contacted in another chamber 56 with fresh supercritical fluid at $T_H$ but at pressure $P_1$. Passing the resulting fluid-component mixture into a fourth chamber 58 and lowering the temperature to $T_L$ will cause only component A to deposit. Passing the exit gas therefrom to a fifth chamber 60 and raising the temperature to $T_H + \Delta T$ will cause only component B to precipitate out. Higher order systems can be treated analogously, as long as the system components exhibit separable cross-over points. The exit gas from any point in the system also can be shunted to a distillation process or recycled.

Figure 5B:
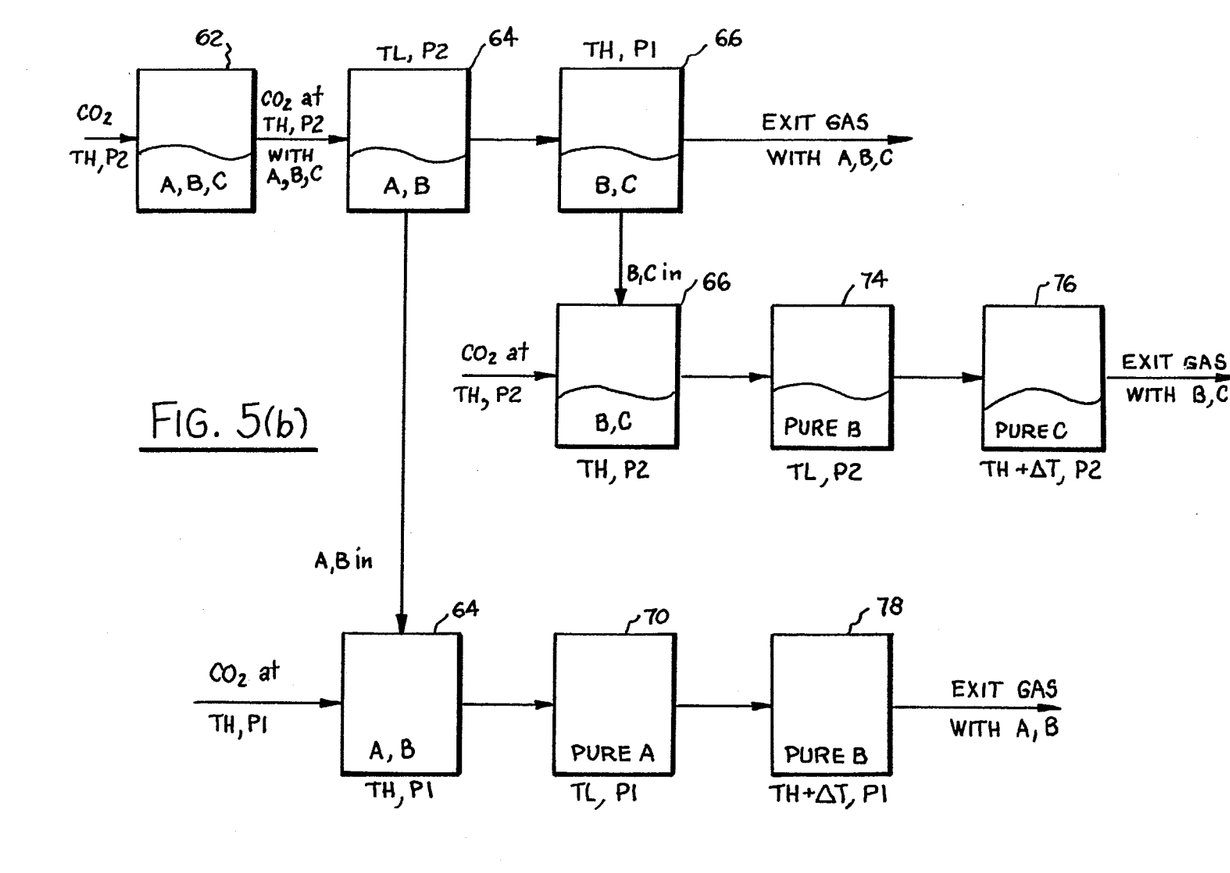

Alternatively, referring to FIG. 5(b), supercritical fluid at a temperature $T_H$ and pressure $P_2$ is contacted with a mixture of A, B and C in a first chamber 62 resulting in a fluid-component mixture. In a another chamber 64, the mixture is cooled to a temperature $T_L$. From FIG. 4, it will be seen that since $P_2$ is in the cross-over regime separating components (A,B) and C, a mixture predominantly of A and B will precipitate out leaving an exit gas rich in C (with reduced amounts of A and B). Upon passing the exit gas into an additional chamber 66, decompression to a pressure $P_1$ and heating to temperature $T_H$ will cause a mixture predominantly of B and C to deposit in said additional chamber. The exit gas from said additional chamber with the remaining quantities of A, B and C can be recycled.

To process the deposited components (A,B) from the other chamber 64, fresh supercritical fluid is passed through at temperature $T_H$ and at pressure $P_1$. The resulting fluid-component mixture is then passed into a separate chamber 70. Lowering the temperature to $T_L$ in the separate chamber will cause only A to deposit therein. The exit gas from the separate chamber 70 can be passed into a distinct chamber 78. Raising the temperature to $T_H + \Delta T$ will cause only B to deposit therein. The exit gas therefrom also can be recycled or shunted to a distillation process.

To process the deposited components (B,C) from the additional chamber 66, fresh supercritical fluid is passed through at temperature $T_H$ and at pressure $P_2$. The resulting fluid-component mixture is then passed into a different chamber 74. Lowering the temperature to $T_L$ will cause only B to deposit therein. Passing the exit gas therefrom to a discrete chamber 76 at temperature $T_H + \Delta T$ will cause only C to deposit therein.

Figure 6:
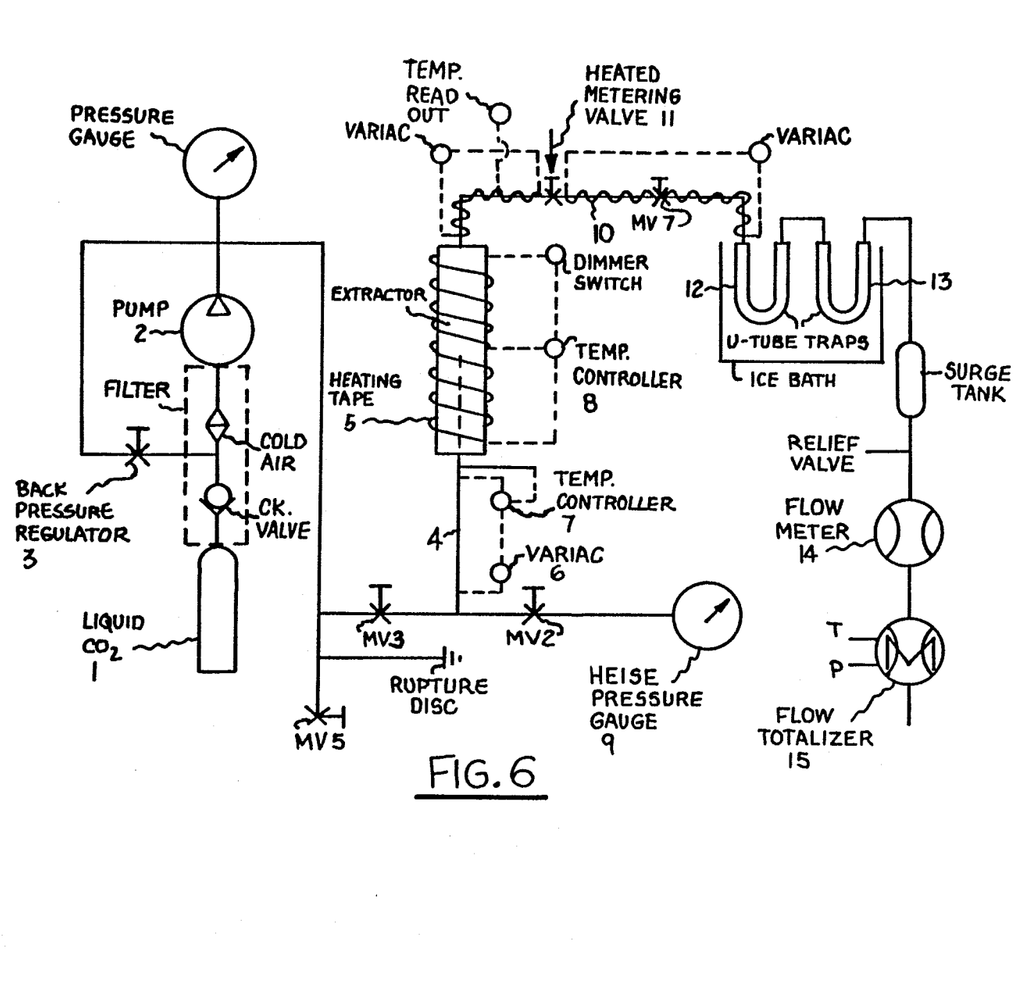
FIG. 6 is a schematic diagram of an apparatus used to measure the solubilities of components in a multi-component system.

Referring to FIG. 6, an apparatus is schematically shown to measure the solubilities of various multi-component systems. Commercially available liquid carbon dioxide (Air Products & Chemicals, 99.8% purity) from a source 1 is compressed to the desired operating pressure by a liquid pump 2. $CO_2$ pressure is controlled suitably to within $\pm 1.5$ bar with a back-pressure regulator valve 3. The high pressure carbon dioxide flows through a preheated section of tubing 4 and into a vertical extraction tube 5.

The preheater 4 can consist of four feet of heating tape wrapped around the tubing carrying the fluid flow. Temperature regulation is provided by an A.C. power control, as with a variac 6, and temperature controller 7 set in on-off mode. The temperature, as measured at the preheater outlet is suitably controlled to within $\pm 1°$ K.

The extraction tube 5 is packed with a uniform mixture consisting of equal volumes of the solid and 3 mm glass beads. The glass beads (not shown) are useful primarily to reduce caking of the solid during operation of the system. In the case of solid mixtures, equal weights of the two solids are combined in a uniform mixture with an equal volume of glass beads. A glass wool plug (not shown) at the outlet of the extraction tube 5 prevents entrainment of the solid.

In the above example, the extraction tube was 1.75 cm in diameter (inside) and 30.5 cm long. It was wrapped with heating tape which was connected to an on-off temperature controller 8. The thermocouple used for the controller's temperature sensor was mounted on the outside wall of the extractor vessel under the heating tape (not shown). The internal temperature was monitored with a thermocouple located in the center of the extraction tube (not shown). The internal temperature was controlled within approximately $\pm 0.5°$ K. A calibrated Heise gauge 9 was used to measure the pressure in the extractor vessel.

The supercritical carbon dioxide and dissolved solid flows out of the extraction tube 5 into a short length of tubing 10 warmed with heating tape to prevent a drop in temperature. The outside wall temperature of this tube 10 is monitored with a thermocouple (not shown) to avoid excessive heating. The dense fluid expands across a heated micrometering valve 11 to about 1 bar. The solids were precipitate in two consecutive tared U-tubes 12,13 immersed in an ice-brine solution. The extractant gas flow rate is measured by a flowmeter 14. The total extractant gas volume is measured with a calibrated meter 15, suitably a Singer dry-test meter 15.

In the above example, the mass of solid collected was found by weighing the tared U-tubes. In the case of a pure solid, knowledge of the total gas volume and weight of the solid collected is sufficient to determine the mole fraction of solid in the supercritical fluid. When dealing with solid mixtures, the composition of the precipitated solid also must be known. NMR spectroscopy can be used to determine mixture compositions. The NMR solvent used can be deuterated chloroform (99.8% pure Aldrich Chemical Co.).

Figure 7:
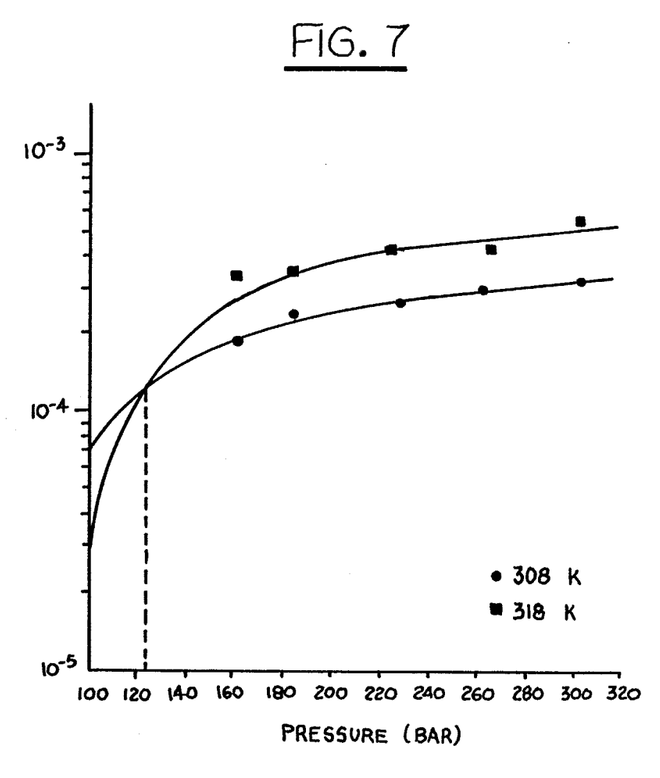
FIG. 7 is a plot of solubility of 1,10-decanediol from a mixture of 1,10-decanediol and benzoic acid in supercritical carbon dioxide measured at 318° K. and 308° K. as a function of pressure.
Figure 8:
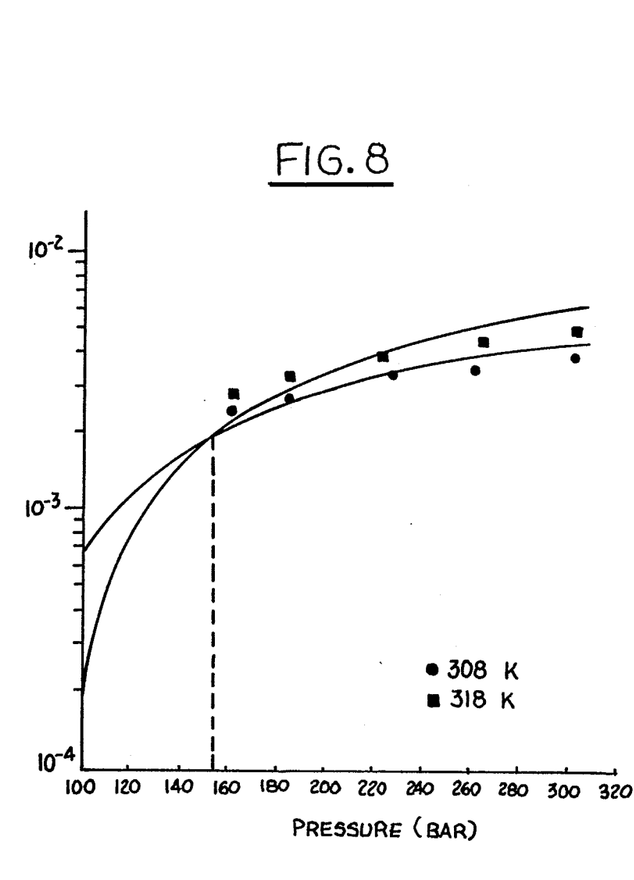
FIG. 8 is a plot of solubility of benzoic acid from a mixture of 1,10-decanediol and benzoic acid in supercritical carbon dioxide at 318° K. and 308° K. as a function of pressure.

In another example, this apparatus was used to measure the solubility of a ternary system consisting of 1,10-decanediol--benzoic acid in supercritical carbon dioxide and the solubility of a binary system consisting of 1,10-decanediol in supercritical carbon dioxide. For the ternary system, temperatures were set at either 318° K. or 308° K. The resulting solubility curves for 1,10-decanediol and for benzoic acid are set forth in FIGS. 7 and 8 respectively. The data points shown for the two components in. FIGS. 7 and 8 show well defined trends including the convergence of the isotherms towards cross-over pressure points.

Figure 9:
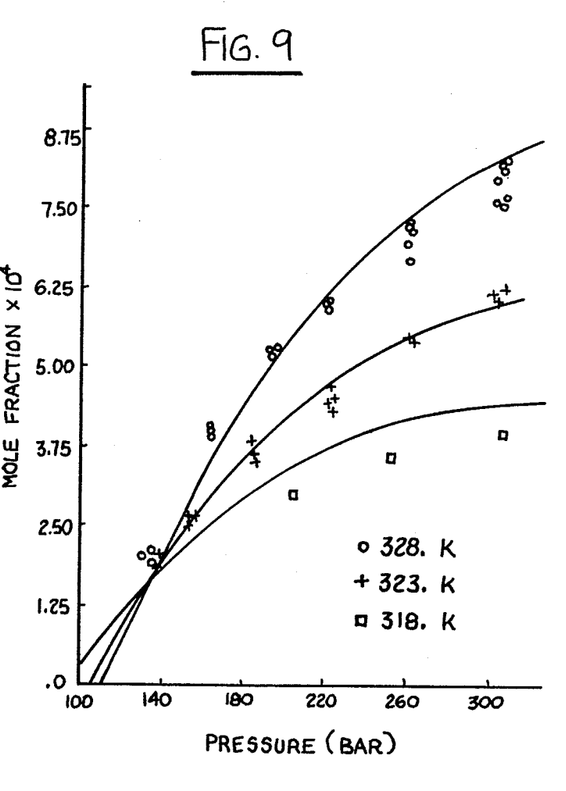
FIG. 9 is a plot of the solubility of 1,10-decanediol in supercritical carbon dioxide at 328° K., 323° K. and 318° K. as a function of pressure.

From the pure component data for carbon dioxide-decanediol presented in FIG. 9, the cross-over pressure for decanediol was found to be approximately 120 bars. Kurnik, et al., J. Chem. Eng. Data, 26:47-51 (1981) have shown the cross-over pressure point for a carbon dioxide-benzoic acid binary system to be approximately 160 bars. Hence, decanediol can be identified with component 1 in FIG. 1 and benzoic acid with component 2. Thus, $P_0$ (the pressure at which true temperature inversion can be expected, see FIG. 2) is to be in the 120-150 bar range.

In fact, one pressure within the cross-over region at which pure decanediol deposits in one system was found to be 132.2 bars. Table 1 sets out the yield of decanediol and benzoic acid using the above described apparatus at $T_H = 318°$ K., $T_L = 308°$ K. and P = 306.8, 228.5, 163.8 and 132.2 bars. Thus, by operating at P = 132.2 bars and decreasing temperature from 318° K. to 308° K., pure decanediol can be obtained.

TABLE 1

Yield-Purity Characteristics for the Separation of 1,10-Decanediol and Benzoic Acid with Supercritical Carbon Dioxide

| Pressure (Bars) | Decanediol Yield** × 10,000 | Benzoic Acid Yield** × 10,000 | Purity Enhancement* Factors for Decanediol in Deposited Phase |
|---|---|---|---|
| 306.8 | 2.29 | 9.76 | 2.13 |
| 228.5 | 1.57 | 6.02 | 2.45 |
| 163.8 | 1.61 | 4.20 | 3.09 |
| 132.2 | 0.225 | 0.00 | ∞*** |

*Purity Enhancement Factor is defined as being the ratio of the mole fractions of decanediol/benzoic acid in the deposited phase to that in the feed.
**Yield is defined as being the ratio of the moles of solid deposited/mole of carbon dioxide in the feed.
***Cross-over regime, pure decanediol deposited.

Finally, supercritical fluids ordinarily are used in their pure state. It is to be noted, however, that small quantities of an entrainer compound, which may be a polar compound such as methanol or acetone, may be doped into the supercritical fluid. This doping has no affect on the mechanics of the present invention except to the extent that such entrainer compounds may increase the solubility of the compounds to be extracted by the doped supercritical fluid. Thus, the invention may be practised with either pure supercritical fluid or with a doped supercritical fluid.

Similarly, it should be apparent that operation of this process at pressures near, but greater than, $P_2$ or near, but less than, $P_1$ will achieve some degree of separation. See FIG. 1. This separation, however, will not be pure, but where purity is not essential, the process need not be limited to operation at pressures between $P_1$ and $P_2$.

Variations and modifications of the herein described method, within the scope of the invention, will undoubtedly, suggest themselves to those skilled in the art. Accordingly, the foregoing description should be taken as illustrative, and not in a limiting sense.

We claim:

1. A process for extracting n pure components from a multi-component system, where n is the number of components in the system, where each of said n components has a cross-over pressure point different from the other components thereby resulting in a range of cross-over pressure points from a highest cross-over pressure point through a next highest cross-over pressure point to lower cross-over pressure points, and where said cross-over pressure point for any n component comprises a pressure being defined on a plot of component solubility versus pressure where temperature isotherms for said component cross, which comprises the steps of
   (1) passing a supercritical fluid through a first enclosed region, said region containing said multi-component system, at a first temperature sufficient to maintain the supercritical fluid in its supercritical state and at a pressure near a cross-over pressure point of any component present in said system thereby generating a fluid component mixture,
   (2) passing said fluid-component mixture from said first enclosed region into a second enclosed region,
   (3) changing said temperature to a second temperature in said second enclosed region to change the solubility of all components in said mixture having different cross-over pressure points causing said components to deposit in said second enclosed region,
   (4) drawing off the remaining fluid-component mixture and passing said mixture into a third enclosed region,
   (5) changing the temperature in said third enclosed region to said first temperature plus an incremental factor causing only the component present in said remaining mixture near the cross-over pressure point to deposit therein,
   (6) drawing off the remaining fluid-component mixture, and
   (7) repeating steps 1-5 on the components deposited in step 3 until all n components have been purified.

2. The process according to claim 1 wherein said supercritical fluid is pure and is selected from the group consisting of hydrocarbons, methylated halogens and inorganic compounds.

3. The process according to claim 2 wherein the supercritical fluid is an inorganic compound.

4. The process according to claim 3 wherein the supercritical fluid is carbon dioxide.

5. The process according to claim 1 wherein the components are liquids.

6. The process according to claim 1 wherein the components are solids.

7. The process according to claim 1 wherein n is equal to two.

8. The process according to claim 7 wherein the first solid is 1,10-decanediol, the second solid is benzoic acid and the supercritical fluid is pure carbon dioxide.

9. The process according to claim 1 wherein said first temperature is 318° K.

10. The process according to claim 1 wherein the second temperature is 308° K.

11. The process according to claim 1 wherein the difference between the first and second temperatures is 10° K.

12. The process according to claim 1 wherein the drawn-off fluid from step (6) is recycled to said first enclosed region after being returned to the appropriate temperature and/or pressure.

13. The process according to claim 1 wherein the drawn-off fluid from step (6) is passed onto a secondary process such as distillation.

14. A process for extracting n pure components from a multi-component system, where each of said n components exhibits a cross-over pressure point different from the other components thereby resulting in a range of cross-over pressure points from a highest cross-over pressure point through a next highest cross-over pressure point to lower cross-over pressure points, and where said cross-over pressure point for any n component comprises a pressure being defined on a plot of component solubility versuses pressure where temperature isotherms for said component cross, which comprises the steps of: (1) passing a supercritical fluid through an initial chamber, said initial chamber containing said multi-component system, at a first temperature sufficient to maintain the supercritical fluid in its supercritical state and at a pressure, said pressure being less than the highest cross-over pressure but greater than the next highest cross-over pressure point for any n component of said multi-component system, thereby generating a fluid-component mixture; (2) passing said mixture from said initial chamber to another chamber; (3) decreasing said temperature to a second temperature to decrease the solubility of the component or components having cross-over pressure points lower than said pressure causing said component or components to deposit in said other chamber; (4) further processing said component or components and n (5) drawing off said remaining mixture.

15. The process according to claim 14 wherein said further processing comprises the steps of passing supercritical fluid through said other chamber containing said component or components deposited at said first temperature but at pressure less than the highest cross-over pressure point of the deposited components, passing said fluid component mixture into a separate chamber, decreasing the temperature in said separate chamber to said second temperature causing the component or components with the next lower cross-over pressure points to deposit in said separate chamber, and drawing off the remaining fluid.

16. The process according to claim 16 wherein said drawn-off fluid is passed into a distinct chamber at the same pressure but at said first temperature plus an incremental factor causing the component or components with the lower cross-over pressure points to deposit therein, and the remaining fluid is drawn-off.

17. The process according to claim 14 wherein said drawn-off fluid is passed into an additional chamber at a different pressure, said different pressure being below the next lowest cross-over pressure point of the remaining components, but at said first temperature causing said remaining component or components with higher cross-over pressure points to deposit in said additional chamber, and the said remaining fluid is drawn-off.

18. The process according to claim 17 wherein supercritical fluid is passed through said additional chamber containing said deposited components at said first temperature but at pressure less than the highest cross-over pressure point of the deposited components, passing said fluid component mixture into a different chamber, decreasing the temperature in said different chamber to said second temperature causing the component or components with lower cross-over pressure points to deposit into said different chamber, and drawing off the remaining fluid.

19. The process according to claim 18 wherein said drawn-off fluid is passed into a discrete chamber at the same pressure but at said first temperature plus an incremental factor causing the component or components with the higher cross-over pressure points to deposit therein, and the remaining fluid is drawn-off.

20. The process according to claim 14 wherein the steps of claim 15 are repeated until the components have been purified.

21. The process according to claim 14 wherein said supercritical fluid is pure and is selected from the group consisting of hydrocarbons, methylated halogens and inorganic compounds.

22. The process according to claim 21 wherein the supercritical fluid is an inorganic compound.

23. The process according to claim 22 wherein the supercritical fluid is carbon dioxide.

24. The process according to claim 14 wherein the difference between the first and second temperatures is 10° K.

25. The process according to claim 1 wherein the supercritical fluid is doped with a small quantity of an entrainer.

26. The process according to claim 14 wherein the supercritical fluid is doped with a small quantity of an entrainer.

27. The process according to claim 1 wherein the enclosed regions comprise separate chambers.

28. The process according to claim 1 the pressure in step 1 is less than the highest cross-over pressure point of any component in said system and greater than the next highest cross-over pressure point in said system.

29. The process according to claim 28 wherein the change in temperature in step 3 comprises a decrease in temperature causing a decrease in the solubility of all components in said mixture having lower cross-over pressure points to deposit.

30. The process according to claim 29 wherein the temperature change in step 5 comprises an increase in temperature causing only the component in said remaining mixture with the highest cross-over pressure point to deposit.

* * * * *